US012620485B2

(12) United States Patent
Song et al.

(10) Patent No.: US 12,620,485 B2
(45) Date of Patent: *May 5, 2026

(54) ENCODED GRAPHICAL MODELING SYSTEM AND METHOD FOR MATCHING PATIENTS OR MEMBERS NEEDING A PARTICULAR MEDICAL PROCEDURE OR OTHER HEALTH INTERVENTION WITH HEALTHCARE FACILITIES OR PROVIDERS

(71) Applicant: Humana Inc., Louisville, KY (US)

(72) Inventors: Yongjia Song, Louisville, KY (US);
Peyman Yousefian, Frederick, MD (US); Rajiv Kumar Gumpina, Louisville, KY (US); Sravya Etlapur, Rochester, MN (US); Nataley Savanah Kennedy, Lexington, MA (US); Brandi Sambola, Gonzales, LA (US); Rohan Vohra, Louisville, KY (US)

(73) Assignee: Humana Inc., Louisville, KY (US)

( * ) Notice: Subject to any disclaimer, the term of this patent is extended or adjusted under 35 U.S.C. 154(b) by 642 days.

This patent is subject to a terminal disclaimer.

(21) Appl. No.: 17/978,677

(22) Filed: Nov. 1, 2022

(65) Prior Publication Data

US 2024/0145084 A1     May 2, 2024

(51) Int. Cl.
*G16H 50/20* (2018.01)
(52) U.S. Cl.
CPC .................................. *G16H 50/20* (2018.01)
(58) Field of Classification Search
None
See application file for complete search history.

(56) References Cited

U.S. PATENT DOCUMENTS

| | | | |
|---|---|---|---|
| 9,438,650 B2 | 9/2016 | Serena | |
| 9,792,658 B1 * | 10/2017 | Vijendra | ................ G06Q 50/01 |
| 10,216,902 B2 | 2/2019 | Vesto et al. | |
| 10,318,584 B2 | 6/2019 | Kloke et al. | |
| 11,080,333 B2 | 8/2021 | Sexton et al. | |
| 2020/0357507 A1 * | 11/2020 | Blalock | ................ G16H 10/60 |

(Continued)

OTHER PUBLICATIONS

Z. Liu, X. Li, H. Peng, L. He and p. S. Yu, "Heterogeneous Similarity Graph Neural Network on Electronic Health Records, " 2020 IEEE International Conference on Big Data (Big Data), Atlanta, GA, USA, 2020, pp. 1196-1205, doi: 10.1109/BigData50022. 2020.9377795. (Year: 2020).*

(Continued)

*Primary Examiner* — Devin C Hein
(74) *Attorney, Agent, or Firm* — Standley Law Group LLP; Jeffrey S. Standley; James L. Kwak

(57) ABSTRACT

A system and method for using a graph-based data structure to capture complex relations between different healthcare entities, analyze and mine healthcare data. The system sets up a framework for analyzing and mining historical healthcare data to help clinical patients and practitioners to guide care and make early decisions for interventions. More particularly, the system and method use graph embedding and machine learning modeling to process healthcare data in order to match member/patients with healthcare facilities or providers for performing a particular medical procedure or other health intervention needed by the patient.

9 Claims, 10 Drawing Sheets

(56)                    References Cited

U.S. PATENT DOCUMENTS

2023/0085697 A1 *   3/2023   Bulu ..................... G16H 10/60
                                                      705/3
2023/0395211 A1 *   12/2023  Englehart ............. G16H 40/67

OTHER PUBLICATIONS

Wang et al., Explainable Reasoning over Knowledge Graphs for Recommendation, 2018, arXiv:1811.04540, https://doi.org/10.48550/arXiv.1811.04540 (Year: 2018).*

* cited by examiner

Figure 2

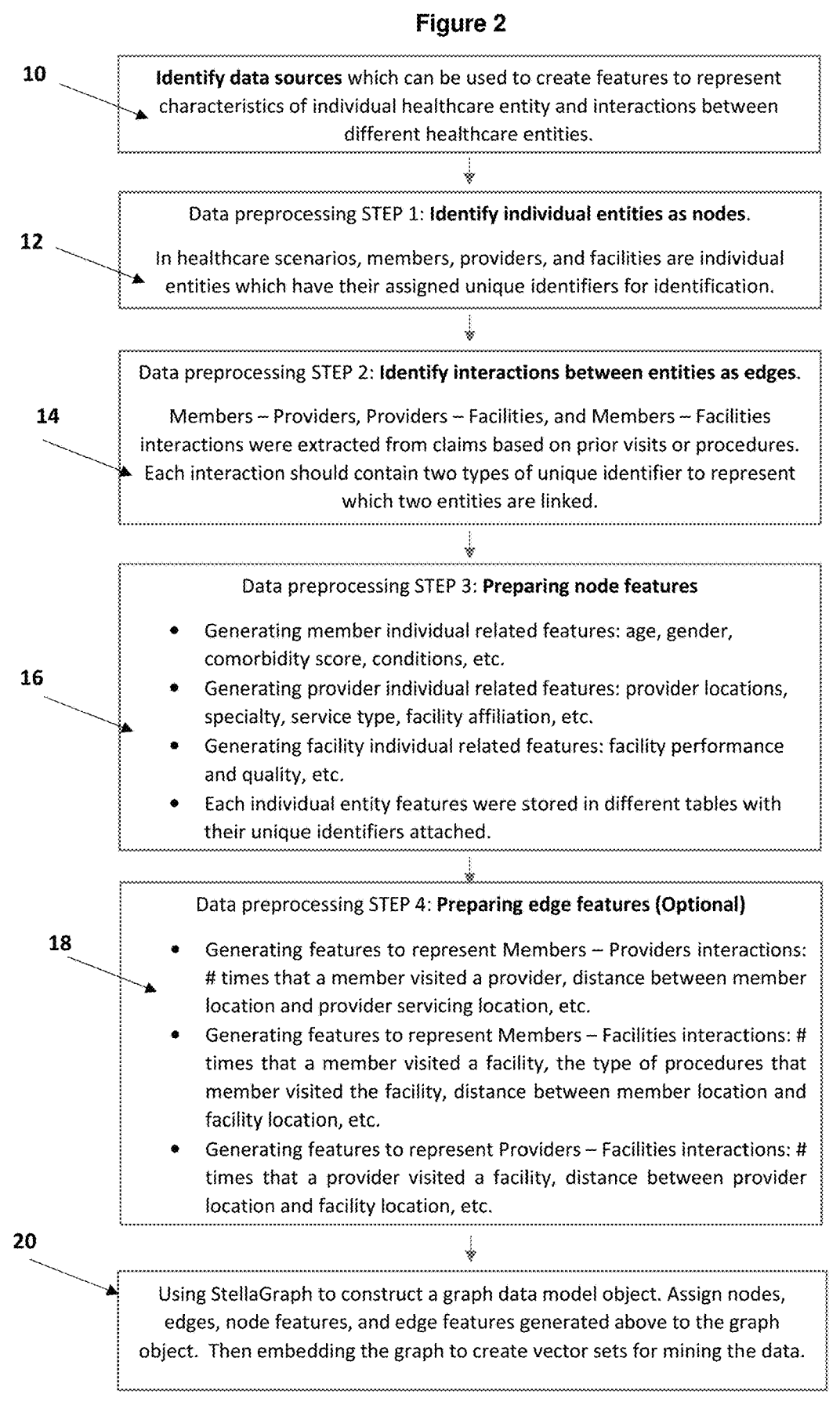

10 → Identify data sources which can be used to create features to represent characteristics of individual healthcare entity and interactions between different healthcare entities.

12 → Data preprocessing STEP 1: Identify individual entities as nodes.

In healthcare scenarios, members, providers, and facilities are individual entities which have their assigned unique identifiers for identification.

14 → Data preprocessing STEP 2: Identify interactions between entities as edges.

Members – Providers, Providers – Facilities, and Members – Facilities interactions were extracted from claims based on prior visits or procedures. Each interaction should contain two types of unique identifier to represent which two entities are linked.

16 → Data preprocessing STEP 3: Preparing node features

- Generating member individual related features: age, gender, comorbidity score, conditions, etc.
- Generating provider individual related features: provider locations, specialty, service type, facility affiliation, etc.
- Generating facility individual related features: facility performance and quality, etc.
- Each individual entity features were stored in different tables with their unique identifiers attached.

18 → Data preprocessing STEP 4: Preparing edge features (Optional)

- Generating features to represent Members – Providers interactions: # times that a member visited a provider, distance between member location and provider servicing location, etc.
- Generating features to represent Members – Facilities interactions: # times that a member visited a facility, the type of procedures that member visited the facility, distance between member location and facility location, etc.
- Generating features to represent Providers – Facilities interactions: # times that a provider visited a facility, distance between provider location and facility location, etc.

20 → Using StellaGraph to construct a graph data model object. Assign nodes, edges, node features, and edge features generated above to the graph object. Then embedding the graph to create vector sets for mining the data.

Figure 5

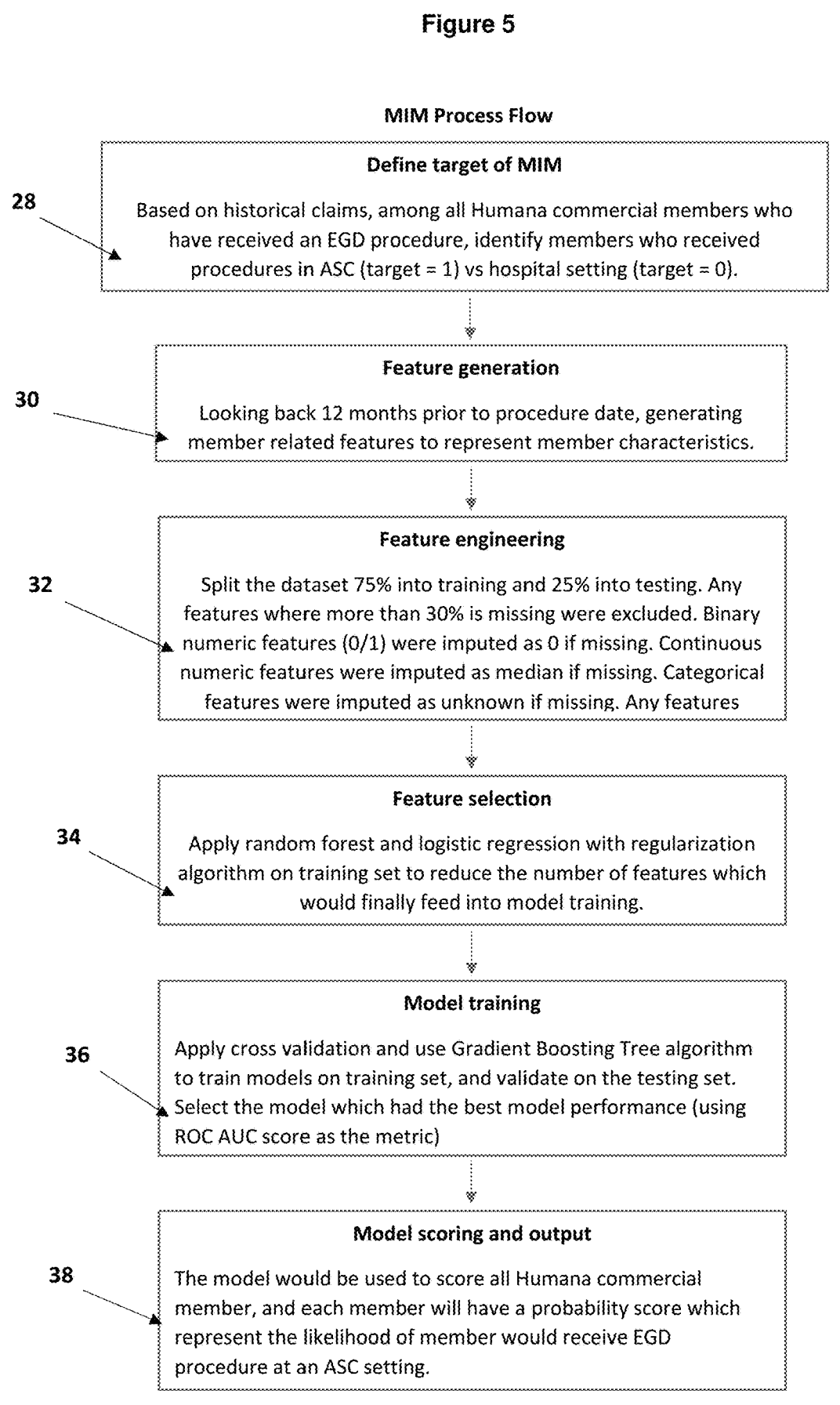

MIM Process Flow

Define target of MIM

28

Based on historical claims, among all Humana commercial members who have received an EGD procedure, identify members who received procedures in ASC (target = 1) vs hospital setting (target = 0).

Feature generation

30

Looking back 12 months prior to procedure date, generating member related features to represent member characteristics.

Feature engineering

32

Split the dataset 75% into training and 25% into testing. Any features where more than 30% is missing were excluded. Binary numeric features (0/1) were imputed as 0 if missing. Continuous numeric features were imputed as median if missing. Categorical features were imputed as unknown if missing. Any features

Feature selection

34

Apply random forest and logistic regression with regularization algorithm on training set to reduce the number of features which would finally feed into model training.

Model training

36

Apply cross validation and use Gradient Boosting Tree algorithm to train models on training set, and validate on the testing set. Select the model which had the best model performance (using ROC AUC score as the metric)

Model scoring and output

38

The model would be used to score all Humana commercial member, and each member will have a probability score which represent the likelihood of member would receive EGD procedure at an ASC setting.

Figure 6

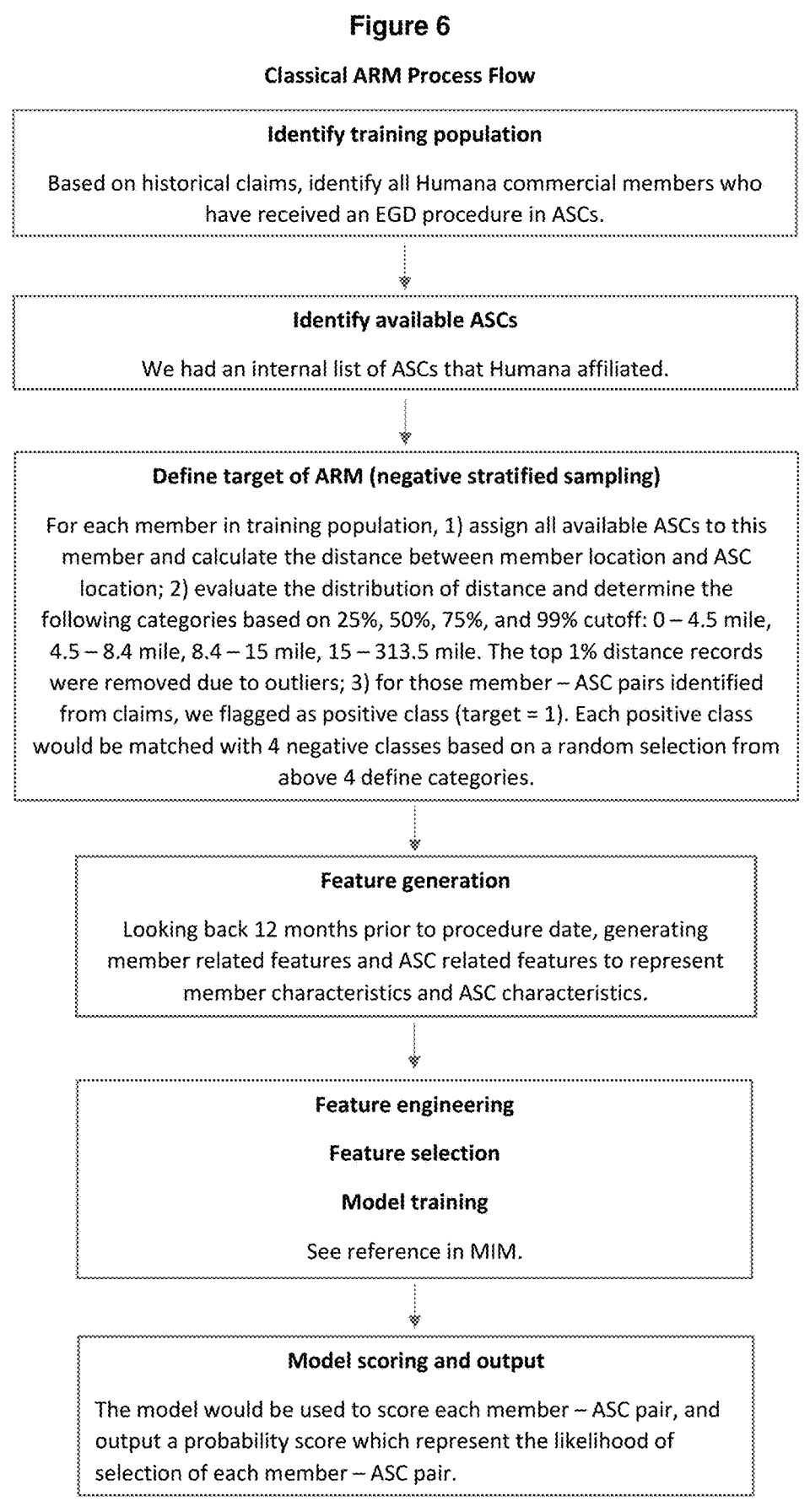

Classical ARM Process Flow

---

Identify training population

Based on historical claims, identify all Humana commercial members who have received an EGD procedure in ASCs.

---

Identify available ASCs

We had an internal list of ASCs that Humana affiliated.

---

Define target of ARM (negative stratified sampling)

For each member in training population, 1) assign all available ASCs to this member and calculate the distance between member location and ASC location; 2) evaluate the distribution of distance and determine the following categories based on 25%, 50%, 75%, and 99% cutoff: 0 – 4.5 mile, 4.5 – 8.4 mile, 8.4 – 15 mile, 15 – 313.5 mile. The top 1% distance records were removed due to outliers; 3) for those member – ASC pairs identified from claims, we flagged as positive class (target = 1). Each positive class would be matched with 4 negative classes based on a random selection from above 4 define categories.

---

Feature generation

Looking back 12 months prior to procedure date, generating member related features and ASC related features to represent member characteristics and ASC characteristics.

---

Feature engineering

Feature selection

Model training

See reference in MIM.

---

Model scoring and output

The model would be used to score each member – ASC pair, and output a probability score which represent the likelihood of selection of each member – ASC pair.

Figure 7A

Graph Version ARM Process Flow

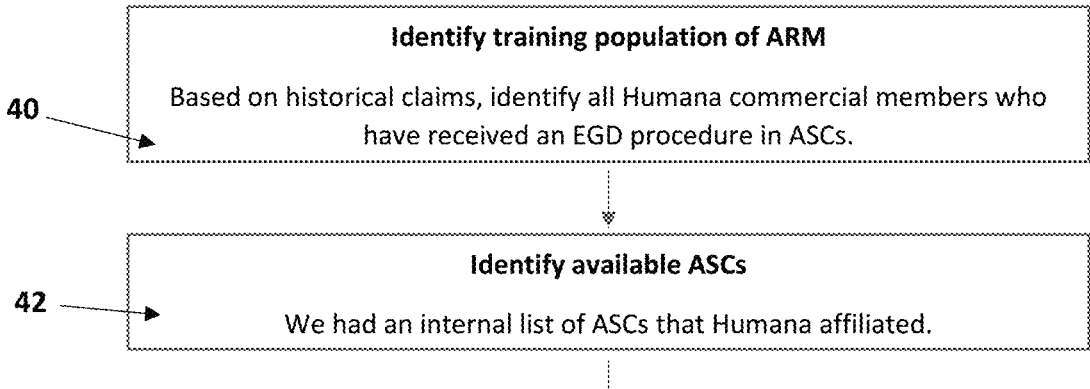

> Identify training population of ARM
>
> Based on historical claims, identify all Humana commercial members who have received an EGD procedure in ASCs.

40

> Identify available ASCs
>
> We had an internal list of ASCs that Humana affiliated.

42

> Define target of ARM (negative stratified sampling)
>
> For each member in training population, 1) assign all available ASCs to this member and calculate the distance between member location and ASC location; 2) evaluate the distribution of distance and determine the following categories based on 25%, 50%, 75%, and 99% cutoff: 0 – 4.5 mile, 4.5 – 8.4 mile, 8.4 – 15 mile, 15 – 313.5 mile. The top 1% distance records were removed due to outliers; 3) for those member – ASC pairs identified from claims, we flagged as positive class (target = 1). Each positive class would be matched with 4 negative classes based on a random selection from above 4 define categories.

44

> Data preprocessing STEP 1: Identify individual entities as nodes.
>
> Members who had EGD procedures in ASCs identified from claims and all Humana affiliated ASCs are individual entities in this use case. Each individual entity had their assigned unique identifiers for identification.

46

> Data preprocessing STEP 2: Identify interactions between entities as edges.
>
> Interactions have been identified based on target definition phase. Iterations consisted of positive interactions between members and their visited ASCs and negative interactions between members and their stratified randomly assigned ASCs. Each interaction should contain two unique identifiers to represent which member and which ASC were linked.

50

Data preprocessing STEP 3: Preparing node features

- Generating member individual related features: age, gender, comorbidity score, conditions, etc.
- Generating facility individual related features: facility performance and quality, etc.
- Each individual entity features were stored in different tables with their unique identifiers attached.

52

Using StellaGraph to construct a graph data model object. Pass above defined nodes, edges, and node features using StellaGraph function from stellagraph package to the graph

54

Randomly split graph object into 75% training set (train graph) and 25% test set (test

56

Define parameters and hyperparameters for further model run.

For example: batch_size = 512 determines the number of samples that will be passed through to the model at one time; epochs = 20 defines the number times that the learning algorithm will work through the entire training dataset; num_samples = [8, 4] defines numbers of neighbor samples will be mapped in each of the two HinSage layers; hinsage_layer_sizes = [32, 8] defines number of the neurons in each of the two HinSage layers; dropout = 0.5 represents a randomly selected neurons are ignored during training; learning_rate = 1e-2 determines the step size at each iteration while moving toward a minimum of a loss function

58

Create the link mappers for sampling and sending training and testing data to the model using HinSAGELinkGenerator function from stellagraph package. The link mappers will take minibatches of member - ASC links, sample 2-hop subgraphs, and feed them together with their link label (1/0) to the input layer of the HinSAGE model.

60

Specify a two-layer HinSAGE model layer using HinSAGE function from stellagraph package. The HinSAGE model layer will take the output of link mappers and produce vector output based on the hinsage_layer_size parameter we specified previously.

Figure 7C

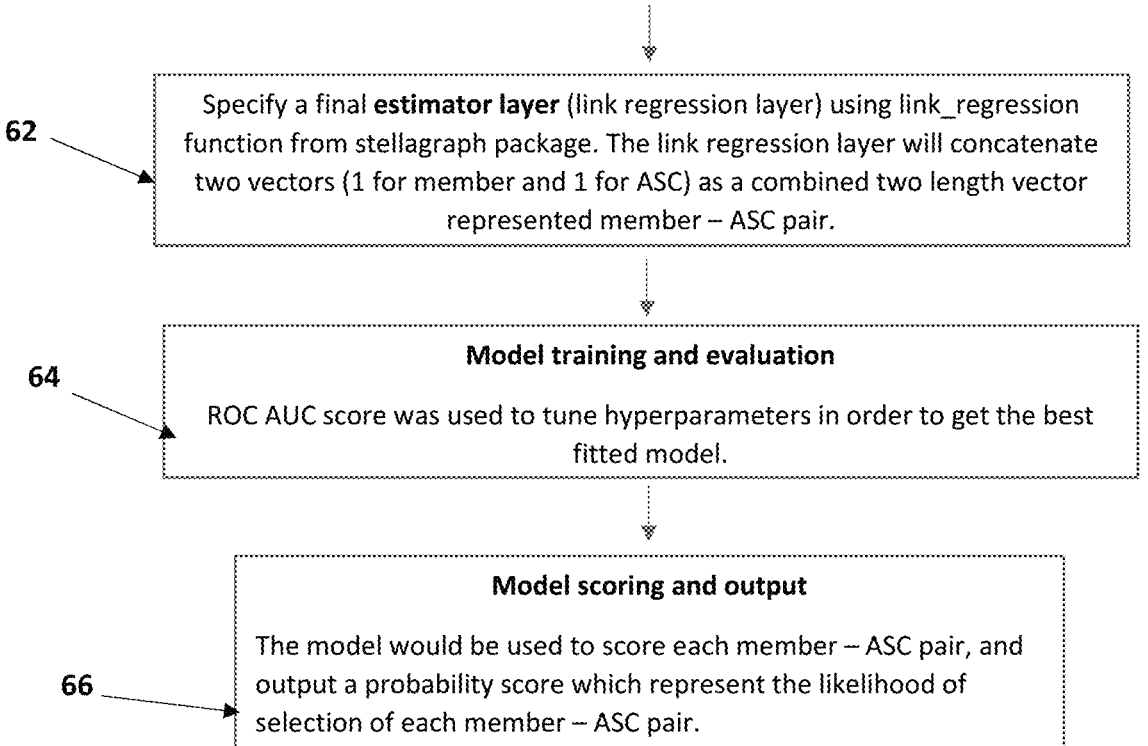

62

Specify a final estimator layer (link regression layer) using link_regression function from stellagraph package. The link regression layer will concatenate two vectors (1 for member and 1 for ASC) as a combined two length vector represented member – ASC pair.

64

Model training and evaluation

ROC AUC score was used to tune hyperparameters in order to get the best fitted model.

66

Model scoring and output

The model would be used to score each member – ASC pair, and output a probability score which represent the likelihood of selection of each member – ASC pair.

68

70

ENCODED GRAPHICAL MODELING SYSTEM AND METHOD FOR MATCHING PATIENTS OR MEMBERS NEEDING A PARTICULAR MEDICAL PROCEDURE OR OTHER HEALTH INTERVENTION WITH HEALTHCARE FACILITIES OR PROVIDERS

BACKGROUND OF THE INVENTIVE FIELD

The present invention is directed to a system and method for using a graph-based framework and structure to capture complex relations between different healthcare entities. The analysis and data mining of rich amounts of interactions between healthcare entities can help clinical practitioners to guide care and make early decisions for interventions. More particularly, the present invention uses graph embedding and machine learning to process healthcare data in order to match member/patients with healthcare facilities or healthcare providers for performing a particular medical procedure or other health intervention needed by the member/patient.

The standardization and sharing of massive amounts of healthcare data enables data-driven analysis using machine learning to solve healthcare problems. In recent years, massive healthcare artificial intelligence (AI) applications have been proposed such as the prediction of medical conditions and disease. In order to maximize the benefits of AI models and capture the relationships between multiple health entities, a graph structure should be established so that graph embedding can then be applied.

Healthcare data usually includes administrative claims, demographics information, diagnosis, conditions, treatments, prescriptions, provider information, hospitalization, insurance, etc. Various entities are involved under healthcare settings: patients, physicians, hospital, other health facility, etc. Building the connection between these entities will play a significant role in lowering down data storage and organization efforts and shedding light in providing better answers for solving healthcare related questions or problems.

Graph analytics, also called network analysis, is the analysis of relationships among multiple entities. In recent years, graph analytics has been applied in various areas, such as resource management, fraud detection, social network analysis, etc. A graph is composed of a set of nodes and a set of edges. FIG. 1 illustrates an example graph comprised of nodes and edges. Nodes can represent different entities, and edges can represent the relationship between a pair of nodes.

Graph embedding is a technique to transform a graph to a vector or set of vectors. It can capture the information of graph topology, node attributes and neighborhood attributes. One key advantage of applying graph embedding is to convert a complex graph data model into a lower dimensional space which can maximally preserve graph structure and information.

The embedding process converts particular input data to be analyzed into a computer-readable vector format. Once embedded, learning for tasks such as disease prediction can be carried out.

The particulars of the embedding process has a significant impact on the performance of the model for future analysis and tasks, and it is important for a quality model to be developed that reflects the accuracy of the data and relationships.

In one practical application of the invention, the framework and processes of the present invention may be used to predict the possibility of clinicians choosing a particular healthcare facility or provider for patients needing a particular medical procedure (e.g., Esophagogastroduodenoscopy (EGD)) and to provide a recommendation for a particular healthcare facility (e.g., hospital, Ambulatory Surgery Center (ASC), clinic, urgent care centers, etc.) or provider.

SUMMARY OF THE GENERAL INVENTIVE CONCEPT

In one embodiment of the invention, the invention is comprised of: a system for predicting and recommending a particular healthcare facility or provider for those members or patients needing a particular medical procedure or other health intervention, the system comprising: a database for storing historical claims data; a plurality of concatenated vectors each comprised of a first member vector and either a first healthcare facility vector or provider vector concatenated together, wherein each of the plurality of concatenated vectors represents either a member-healthcare facility pair or member-provider pair; a computer processor; a non-transitory computer-readable medium storing instructions that when executed by the computer processor cause the computing device to perform the steps of:

a. applying a deep learning model to the plurality of concatenated vectors; and b. determining the probability that each member-healthcare facility pair or member-provider pair will be selected for the particular medical procedure or other health intervention.

In one embodiment, the graph is further comprised of:

a heterogeneous graph extracted from the historical claims data, the graph comprised of at least two types of nodes selected from the group comprising a member node, a healthcare facility node, and a provider node, the heterogeneous graph further comprising a plurality of edges each representing a positive class, and a plurality of edges each representing a negative class, wherein each edge representing a positive class connects one member node to one healthcare facility node or provider node that the one member has a previous connection or visit with and wherein each edge representing a negative class connects one member node to one healthcare facility node or provider node that the one member does not have a previous connection or visit with.

The present invention is also preferably comprised of:

a first model used to score the likelihood that each member would receive the particular medical procedure or other health intervention at the particular type of healthcare facility or with one of the providers before determining the probability that each member-healthcare facility pair or member-provider pair will be selected for the particular medical procedure or other health intervention.

The non-transitory computer-readable medium stores instructions that when executed by the computer processor cause the computing device to perform the steps of:

c. assigning all available healthcare facilities or providers to each member;

d. determining a distance between each member location and each healthcare facility location or provider location;

e. grouping each distance between each member location and each healthcare facility location or provider location into a predetermined number of categories based on the determined distance;

f. matching each edge representing a positive class with one randomly selected edge representing a negative class from each of the categories; and g. preparing the graph.

In one example embodiment, the particular medical procedure needed is Esophagogastroduodenoscopy (EGD) and the particular healthcare facility is an Ambulatory Surgery Center (ASC).

The output of the present invention can be displayed at a graphical user interface comprised of a first region for entering a zipcode for a particular patient or member, and a second region for listing recommended healthcare facilities or providers for performing the particular medical procedure or other health intervention; and wherein the system is configured to receive user input of a numeric zipcode, to determine the probability that each member-healthcare facility pair or member-provider pair will be selected for the particular medical procedure or other health intervention, and to populate the second region with the recommended healthcare facilities or providers.

The foregoing and other features and advantages of the present invention will be apparent from the following more detailed description of the particular embodiments, as illustrated in the accompanying drawings.

BRIEF DESCRIPTION OF THE DRAWINGS

In addition to the features mentioned above, other aspects of the present invention will be readily apparent from the following descriptions of the drawings and exemplary embodiments, wherein like reference numerals across the several views refer to identical or equivalent features, and wherein:

FIG. 2 illustrates a flowchart depicting the general process steps for preprocessing data of one embodiment of the present invention for constructing a graph data model object and converting it to a vector (embedding);

FIG. 5 illustrates the process flow for one embodiment of the MIM process;

FIG. 6 illustrates one embodiment of a classical ARM process flow of the present invention;

FIGS. 7A-7C illustrate one example embodiment of the graph version of the ARM process flow in calculating a probability score that represents the likelihood of selection between a member-ASC pair (e.g., probability that a particular ASC would be selected for a member needing an EGD procedure—based on e.g., geographic location, facility quality, and prior utilization pattern)

DETAILED DESCRIPTION OF EXEMPLARY EMBODIMENT(S)

Figure 1:
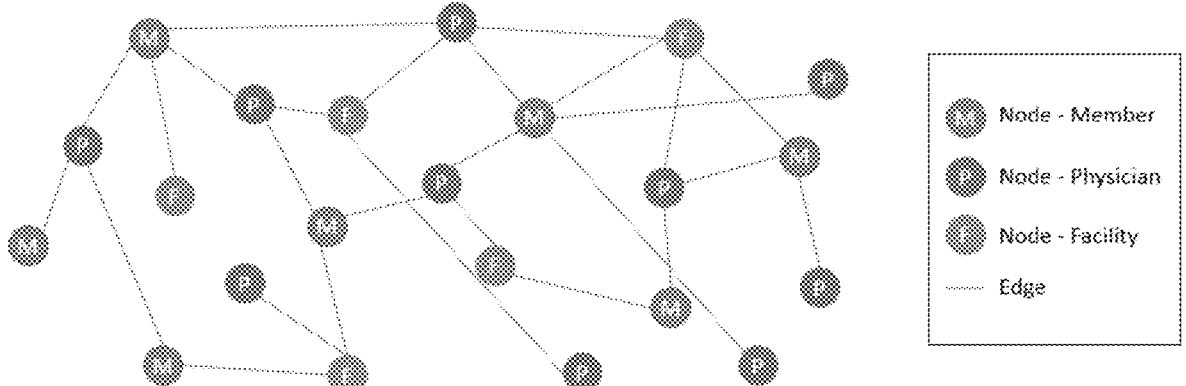
FIG. 1 illustrates an example graph comprised of nodes and edges.

The following detailed description of the example embodiments refers to the accompanying figures that form a part thereof. The detailed description provides explanations by way of exemplary embodiments. It is to be understood that other embodiments may be used having mechanical and electrical changes that incorporate the scope of the present invention without departing from the spirit of the invention.

FIG. 2 illustrates a flowchart depicting the general process steps for preprocessing data of one embodiment of the present invention for constructing a graph data model object and converting it to a vector (embedding). In general, various data sources can be identified and chosen to create features to represent characteristics of individual healthcare entity and interactions between different healthcare entities.

Various types of healthcare related data can be used as inputs to the present invention, for example:

Member/patients data: demographics, locations, conditions (based on ICD 10 codes), treatments and procedures (based on CPT/HCPCS codes), prescriptions (NDC codes and drug categorization), cost and utilization from medical/pharmacy/lab claims, etc.

Provider data: demographics, specialty, service type, locations, hospitals/healthcare facility affiliation, contract with payer, etc.

Hospital/other healthcare facility data: locations, affiliation with providers, specialty, performance and quality, etc.

In a preferred embodiment of the invention, the process outputs a graph object which connects members, providers, and facilities. This graph object can be processed further to fit into different use cases as explained in further detail below. In an example embodiment, the present invention can run off a third-party cloud platform.

In one embodiment of the present invention, the following steps may be taken and applied to different healthcare applications:

1. identify data sources which can be used to create features to represent characteristics of individual healthcare entity and interactions between different healthcare entities 10.

2. preprocess the data as discussed in detail below by identifying individual entities as nodes 12, identify interactions between entities as edges 14, preparing node features 16, and preparing edge features 18;

3. graph the relevant healthcare data to nodes and vector and predetermined feature sets (e.g., using StellaGraph) 20;

4. embed the graph data into vectors using a graph embedding technique (e.g., using GraphSAGE);

5. apply artificial intelligence (AI) machine learning on the vectors to create a model for generating probability scores for different applications (e.g., identifying most likely member-ASC pairs).

In one embodiment of the invention, a framework for site of care prioritization and recommendation is established using the method of the present invention. The invention can be adopted across other procedures or various types of site of care recommendations.

Constant innovation and optimization is needed to meet demands of the healthcare system. Ambulatory surgery centers (ASC) are a model of health care delivery system that sometimes leads to cost savings, flexible scheduling, shorter stays, improved care, and overall improved patient experience. The objective of this use case was to identify patients/members with Esophagogastroduodenoscopy (EGD) which could potentially be safely conducted in an ASC setting and recommending the best fitted ASC to clinicians.

In this example embodiment of the present invention, two AI driven solutions were developed: MIM and ARM. The primary objectives of MIM were predicting the probability of clinicians choosing an ASC for patients needing EGD and providing member level insights. ARM was then aimed at recommending ASCs to clinicians based on geographic location, facility quality, and prior utilization pattern.

Figure 3:
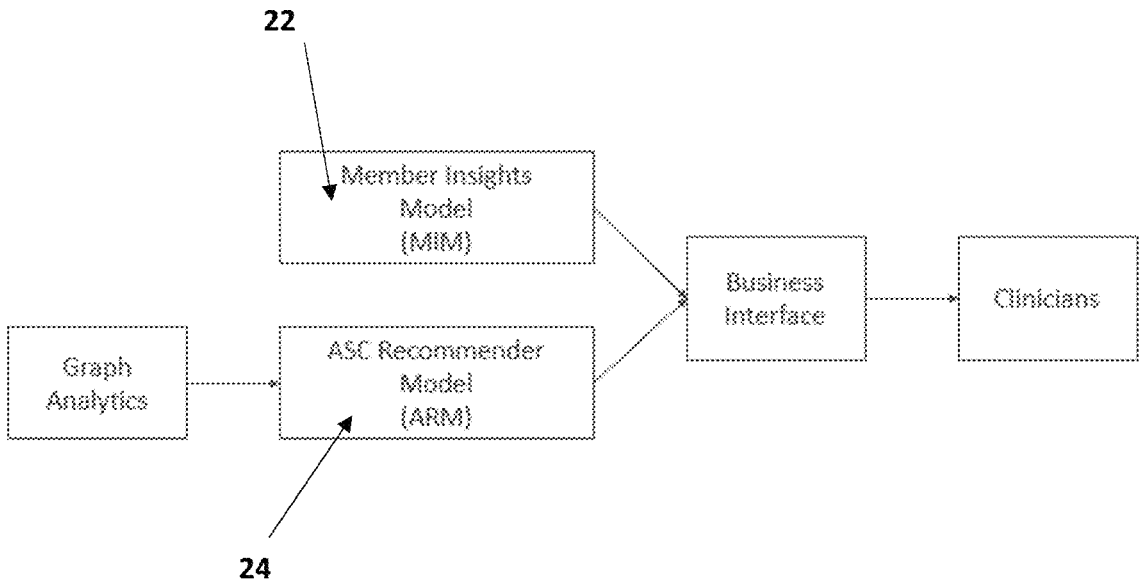
FIG. 3 illustrates a general framework and process flow for one practical application of the present invention—the Member Insights Model (MIM) and ASC Recommender Model (ARM) of the present invention.

FIG. 3 illustrates a general framework and process flow for one practical application of the present invention—the MIM 22 and ARM 24 of the present invention. Initially MIM and ARM were developed using classical machine learning approaches, however these approaches consider multiple healthcare entities independently. Graph analytics was then applied in the ARM to bring the knowledge of relationships between different healthcare entities into an advanced deep learning task to improve site of care recommendation.

In this example practical application of the present invention, the invention is comprised of the following novel features:

A framework for site of care prioritization and recommendation. The present invention can be adopted across other procedures or other types of site of care or provider recommendations.

An innovative way of generating negative samples based on stratified sampling strategy to be used in the ARM model.

Application of a graph-based data structure to capture complex relations between different healthcare entities.

Application of graph embedding algorithms to transform healthcare data by converting complex data and connectivity into a lower dimensional space.

Generation of graph embedding and link prediction for healthcare prediction tasks.

Figure 4:
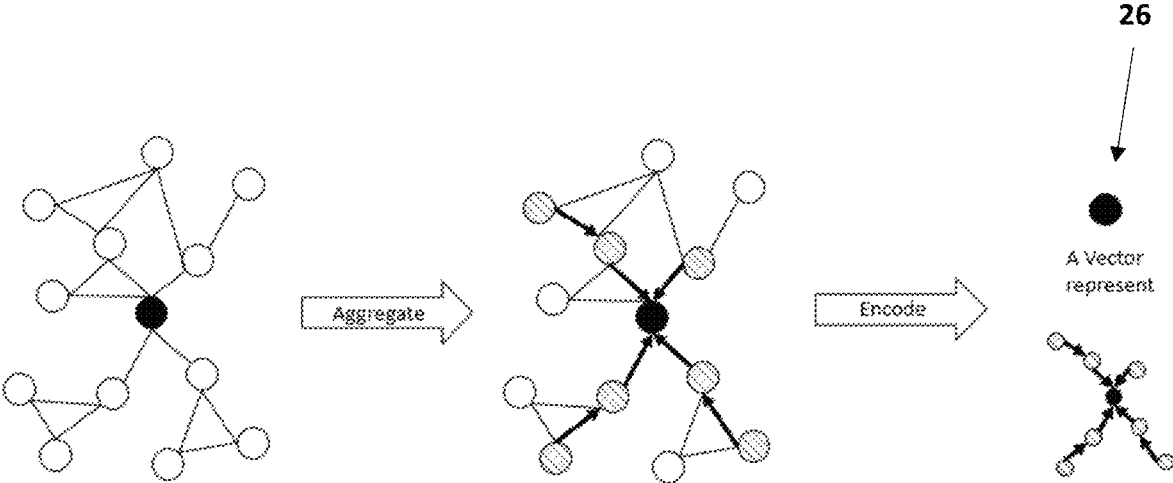
FIG. 4 illustrates a graphical depiction of the graph embedding process for one example embodiment of the present invention.

FIG. 4 illustrates a graphical depiction of the graph embedding process for one example embodiment of the present invention. As illustrated, a node for the particular graph is encoded or embedded into a vector 26 which then can be decoded (e.g., decode neighborhood and node label).

Data inputs for this example embodiment may include:

Member/patients data: demographics, locations, conditions (based on ICD 10 codes), treatments and procedures (based on CPT/HCPCS codes), prescriptions (NDC codes and drug categorization), cost and utilization from medical/pharmacy/lab claims, etc.

ASC facility level data:

Quality metrics data from CMS Ambulatory Surgical Center

Quality Reporting (ASCQR) Program Measures (cms.gov)

Census data (from American Census Bureau, mapped it with ASC zip code)

Cost and utilization data (identified from medical claims and aggregated on ASC level).

Data outputs for the example embodiment may include:

For MIM: A probability score which indicates the likelihood of members finally receiving EGD at an ASC setting.

For ARM: A probability score which indicates the likelihood of selection between each member and ASC pair.

FIG. 5 illustrates the process flow for one embodiment of the MIM process. The steps depicted include: defining a target of the MIM 28, feature generation 30, feature engineering 32, feature selection 34, model training 36, and model scoring and output 38.

In one embodiment of the invention, utilization is a part of the node features, but geographic location is not. For one embodiment of the feature selection process, random forest and logistic regression is applied with regularization algorithm on a training set to reduce the number of features which feeds into model training.

In the example embodiment, the MIM process flow does not use graph techniques to convert the data into nodes and edges. Instead, a classical binary classification approach is used. In this example, the MIM process MIM may be trained on a binary classification using Gradient Boosting Tree algorithm.

FIG. 6 illustrates one embodiment process flow of the present invention using a classical ARM process. In one embodiment of the invention, the classical ARM process is applied as described in FIG. 6. In another embodiment of the invention, a graph version of the ARM process of the present invention can be used in place of the classical ARM process. The baseline classical ARM is preferably trained on a binary classification using Gradient Boosting Tree algorithm.

FIGS. 7A-7C illustrate one example embodiment of the graph version of the ARM process flow in calculating a probability score that represents the likelihood of selection between a member-ASC pair (e.g., probability that a particular ASC would be selected for a member needing an EGD procedure—based on e.g., geographic location, facility quality, and prior utilization pattern). The described processes of the present invention can be similarly applied for members-provider pairs, and for any health intervention needed (as opposed to being limited to EGD procedures).

The steps of this process flow includes the steps of: identifying the training population of the ARM 40, identifying available ASCs 42, defining a target of the ARM (negative stratified sampling) 44, data preprocessing step 1 (identifying individual entities as nodes) 46, data preprocessing step 2 (identifying interaction between entities as edges) 48, data preprocessing step 3 (preparing node features) 50, constructing a graph data model object (e.g., using StellaGraph) 52, randomly splitting graph objects—75% training set and 25% test set 54, defining parameters and hyperparameters for further model runs 56, creating link mappers for sampling and sending training and testing data to the model using 58, for example, a HinSAGELinkGenerator function from the StellaGraph package, specifying a two-layer HinSage model layer to produce a vector output 60, specifying a final estimator layer (e.g., link regression layer) to concatenate two vectors (one for a member and one for an ASC) as a combined two length vector representing a member-ASC pair 62, training and evaluating the model 64, using the model for scoring, and outputting probability scores 66.

As described in FIG. 7A, the present invention uses an innovative way of generating negative samples based on a stratified sampling strategy ("negative stratified sampling"). In other words, to develop a binary classification model to predict if a certain ASC is the best fitted ASC for a member, the process of the present invention uses both positive classes and negative classes from historic claims to indicate if a certain ASC is the best fit (positive target) or not the best fit (negative target).

In other words, for each member in training population, 1) assign all available ASCs to this member and calculate the distance between member location and ASC location; 2) evaluate the distribution of distance and determine the following categories based on 25%, 50%, 75%, and 99% cutoff: 0-4.5 mile, 4.5-8.4 mile, 8.4-15 mile, 15-313.5 mile. The top 1% distance records were removed due to outliers; 3) member—ASC pairs identified from claims were flagged as positive class (target=1). Each positive class is then matched with 4 negative classes based on a random selection from the above 4 defined categories.

For every supervised machine learning task, the present invention recognizes the need for both positive and negative targets (classes). In ARM scenarios, to predict if a member will likely visit a certain ASC, during the model training, it is desirable to collect information on which members visited which ASCs (positive classes), and which members didn't visit which ASCs (negative classes). Claims data will only provide the identities of the members who visited ASCs and which ASCs they visited. Thus, the present invention makes the following assumptions:

i. if a member visited an ASC, it was assumed that ASC was suitable to the member's need or that member wanted to visit that ASC;

ii. if there are other ASCs located around the member that were not visited by the member, then the assumption was made that those ASCs were not suitable for the member's need or that the member did not want to visit that particular ASC.

For example, Member 1 has visited ASC Alpha in the past 12 months, and there are 10 other ASCs located around Member 1 (within 313.5 miles) that he or she has never visited in the past 12 months. In this scenario, the present invention will treat ASC Alpha as a positive class, and, will randomly pick four ASCs (based on distance categorization) out of the 10 other ASCs as negative classes. In other words, one negative ASC was picked randomly from each of the 4 distance categories (categories based on 25%, 50%, 75%, and 99% cutoff: 0-4.5 mile, 4.5-8.4 mile, 8.4-15 mile, 15-313.5 mile).

Thus, there will preferably be five records for Member 1, one with ASC Alpha, and other four with other ASCs. Four negative classes were chosen because it was desirable to have some relative balance between the positive and negative classes. Currently the target rate is around 20% (1 divided (1+4)). Usually, an extremely imbalanced target rate will impact the model performance. The 313.5 mile distance was chosen as maximum distance in this example embodiment, because the present invention recognizes that 99% members would like to visit ASCs located within 313.5 miles of the member.

For this example, Member 1 is a member node, and her node connects with five ASC nodes (one positive ASC, and four negative ASCs). For the edge between Member 1 and the positive ASC class, the present invention attaches label=1 for the edge. For the rest of the four edges connecting Member 1 with each of the four negative ASC nodes, the present invention attaches label=0. In this way, the model will know which ASC that Member 1 visited versus not-visited. Thus, in the present invention, this information is preferably ingested in a graph structure as an edge label.

In the preferred embodiment, an existing/known graph embedding algorithm (e.g., GrapgSAGE) is applied to the graph data to transform the healthcare data by converting complex data and connectivity into a lower dimensional space (vector).

The goal of GraphSAGE is to learn a representation for every node based on some combination of its neighboring nodes. GraphSAGE is a representation learning technique capable of predicting embedding of a new node, without requiring a re-training procedure. To do so, GraphSAGE learns aggregator functions that can induce the embedding of a new node given its features and neighborhood. This is called inductive learning. The GrapgSAGE Algorithm is inductive, while many other graph embedding algorithms are transductive. The use of other algorithms, for unseen nodes, often requires rerunning the whole graph to generate embeddings for the newcomers. In contrast, GraphSAGE is an inductive framework that leverages node attribute information to efficiently generate representations on previously unseen data. It's especially useful for graphs have rich attribute information.

In the ARM use case, a heterogeneous GraphSAGE algorithm was used for the embedding process because: 1) the ARM graph architecture is a heterogeneous graph structure, which has two types of nodes (members and ASCs)—a homogeneous graph structure only has one type of node and one type of edge, which does not fit this use case; 2) an inductive graph algorithm was better for this use case because it has very rich attribute information for nodes, and to learn the pattern of the attribute information from the nodes to generate embeddings for unseen data.

In this example use case, node features such as age, gender, facility performance are used in the model scoring process. The embedding process (e.g., using GraphSAGE) assumes that nodes that reside in the same neighborhood should have similar embeddings. Thus, the first step in the embedding process is to define a sample neighborhood.

The next step is to aggregate feature information from neighbors. Aggregation functions accept a neighborhood as input and combine each neighbor's embedding with weights to create a neighborhood embedding. To learn embeddings with aggregators, embeddings of all nodes are initialized to node features. A neighborhood embedding is created for each node and concatenated it with the existing embedding of the node.

A vector, in its simplest form, can be a series of numbers. For example, $[1, 5, 9, 6, 4, 2]$ is a vector of size 6. A feature vector is a vector representing the features of a particular object. For example, if we have a box B with width, height, and depth, then the feature vector for box B can be represented as B=[width, height, depth]. For a Box B1 with width 6, height 8, and depth 4, the feature vector would be B1=[6, 8, 4]. A graph consists of vertices/nodes and edges. As another example, a graph can represent a social network having nodes are members of the network and the edges connecting them represent their network or "friend" links between members. This graph has node objects (members) that can also have a feature vector containing information about each member such as name, city, job, etc.

For example, assume that a graph has been constructed for ARM and that all nodes were attached with features. The next step is to generate embeddings for all members nodes and ASC nodes. Taking one member as an example, a darkened center circle (e.g., see FIG. 4) in the graph represents a member node. GraphSAGE embedding: 1) will use one of the hyperparameters we specified to sample the neighborhood. For example: num samples=[8, 4] means two layers, 8 samples in first layer, 4 samples in second layer; 2) after determining the neighborhood (a small subgraph), feature information is aggregated from the neighbors (recall that every node can have their own feature vector).

For an example graph, assume V is a member node, and 1,2,3 are three ASC nodes. Member has 5686 features attached, and ASC has 179 features attached. First, averages of all features of these three ASCs in a vector are obtained. Second, this averaged ASC vector and member vector are concatenated together preferably using full concatenation. The member vector preferably has a weight, as does the averaged ASC vector.

This results in a final vector for a member, also represented with the updated vector with neighborhood information. This process is repeated to make sure every member—ASC pair has a vector for member and a vector for an ASC. Finally, the two vectors for each member—ASC pair are combined into one vector as concatenation. This final vector will also multiply a weight matrix to produce a final probability. All weights are preferably learned and updated based on loss function. Machine learning can then be applied to these final vectors to perform needed functions like prediction using the aggregated information. In other words, artificial intelligence (AI) machine learning is applied on the vectors to create a model for generating probability scores (e.g., likelihood of selection for each member-ASC pair).

The present invention uses neural networks or a set of algorithms modeled and designed to recognize patterns in the input data based on a set of rules. These networks associate historical information with new information in order to selectively learn the required information. The learned patterns are stored as a "model" which can then be used to make informed decisions on new data. The network can use stored values or nodes and weights derived from historical data to make predictions on new input data (i.e., also referred to as machine learning).

As explained in the flowchart of FIGS. 7A, 7B, in one example embodiment, the ARM graph invention uses a Keras Deep Learning Model. It is composed by a HinSage model layer (for generating embeddings) and estimator layer using a link regression function (for determining final probability prediction). The Keras model is mature, well supported, and very suitable for the graph invention of the present invention.

Thus, in this example practical application of the invention, the framework and processes of the present invention are used to:

1. MIM process: predict the possibility of clinicians choosing a particular healthcare facility for patients needing a particular medical procedure (e.g., Esophagogastroduodenoscopy (EGD)); and
2. ARM process: provide a recommendation for a particular healthcare facility (e.g., hospital, ASC, clinic, urgent care centers, etc.) for those identified patients.

The present invention as described provides significant advantages over known methods because:

Stratified negative sampling strategy can be applied on any use case which only positive samples are available.

A graph-based structure can be applied on similar healthcare use case which benefits from learning connectivity between different entities.

Graph embedding and link prediction can be utilized on other healthcare AI problems to enrich the architecture and performance.

The approach in this use case can be expanded on other line of business and other procedures which fits into the paradigm The present invention as describes provides significant advantages over known methods because:

a. The approach to generate edges between nodes is unique. In this application, the connection between member and ASCs is extracted from historic medical claims. If a member has visited a certain ASC in the past, a link (edge) is created between this member and the ASC. This specific approach can be also applied to extract edges between member and providers, and provider and ASCs in many other qualified healthcare use cases.
b. The approach to generate negative samples for this link prediction task is unique. In order to predict if a member would select a certain ASC or not, historic data for both classes (yes or no) is acquired to train the model for prediction. We can extract positive classes from medical claims, but there are no negative classes. The specific way to create stratified negative samples were described above.

c. The approach to split the training graph and testing graph is unique in this application. In order to test the model performance of the graph model, the initial graph is split into a training graph and testing graph. A random selection is performed based on member, rather than whole graph connections. For example, if a graph included 100 member nodes, 75 members are randomly selected and the nodes and edges associated with 75 members are assigned as the training set—the rest of the 25 members, with assigned nodes and edges, are used as the testing set.
d. The graph structure is a heterogeneous graph which is composed of two type of nodes (members and facility (e.g., ASC) nodes) and one type of edge. This heterogeneous graph can be further expanded to include providers as an additional node and generate more edges between member—provider and provider—ASCs.

In the example embodiment described, the output of the MIM process is used to identify those patients most likely to receive an EGD procedure at an ASC and then that information is fed into the ARM process to find the most likely ASC for that member. In other words, MIM will be used to identify which members will have a higher likelihood of having EGD in an ASC setting. For those identified members, the ARM of the present invention is used to recommend the best fitted ASCs to these members' providers.

Figure 8:
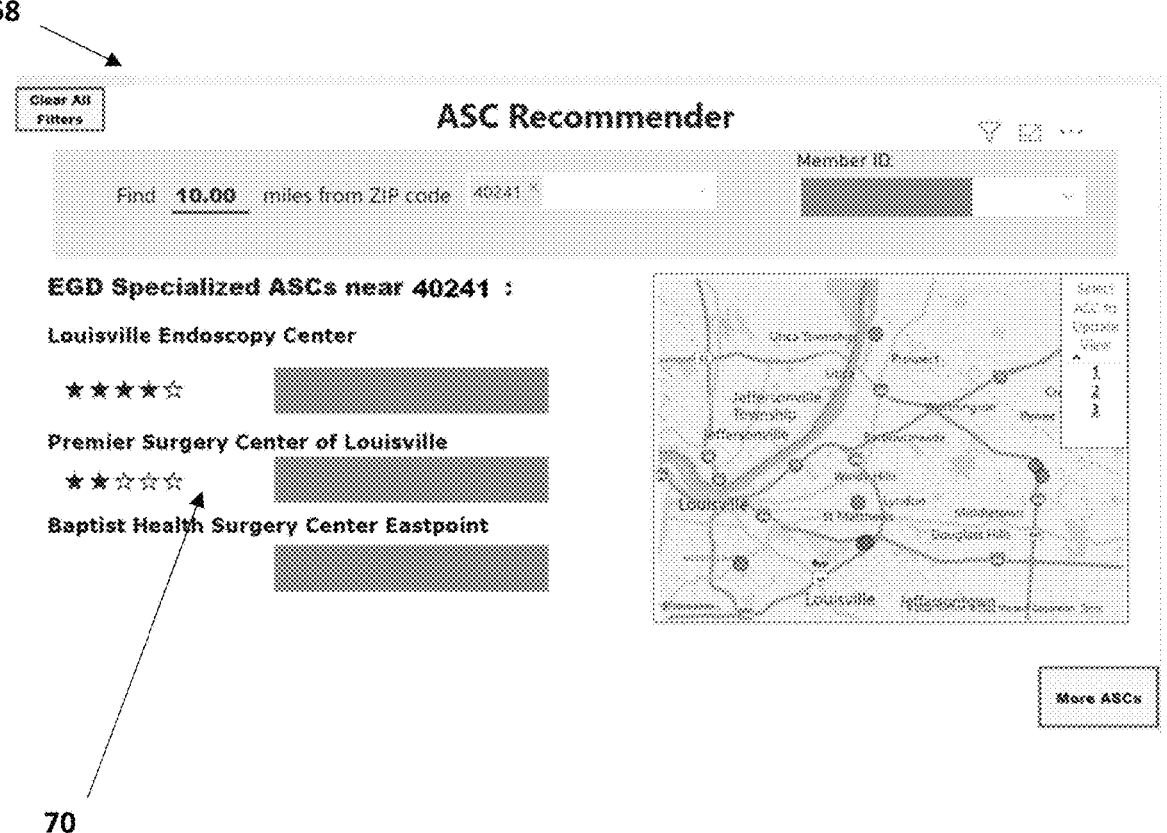
FIG. 8 illustrates one example embodiment of a user interface for displaying the outputs of the present invention.

FIG. 8 illustrates one example embodiment of a user interface 68 for displaying the outputs of the present invention. In one embodiment, a visualization dashboard lays out the ARM model output for presentation to business users. In the example embodiment described, the end users are the providers for those members who will need to have EGDs in an ASC setting. The tool will preferably give providers the flexibility of entering distance and zip code based on their preference after inputting a member ID. The dashboard will layout (recommend) 3 ASCs 70 based on the member, zip code, and distance information, which is backend supported by the ARM. The order of these 3 ASCs is a reflection of model probability scores outputted by the ARM process of the present invention (e.g., ranked by most probable to least). Along with the recommendation, some insights regarding the quality/performance of an ASC, and the past cost and utilization of EGD services between insured members and that ASC may be provided through the user interface. "Members" is defined as members of a health organization such as insureds of a health insurance company. This supplemental information is not relevant to the ARM process, but serves as additional insights to help providers make a decision.

Other examples of practical applications of the present invention include:

Recommendation of site of care to members as opposed to clinicians as previously discussed above. Recommendations may be based on member historic site of care preference, provider historic site of care preference, and member/provider networks etc. For example, if a member is currently visiting a provider who is more likely to conduct surgery in facility A, the invention might recommend facility A to this member based on his doctors' familiarity or affiliation with the facility.

Provider segmentation: providers can be segmented into distinct groups, based on member/provider networks, provider/payer contract, provider/facility affiliation, and historic member/provider engagement. Providers in different groups can then be targeted by intervention programs tailored by their profiles.

Provider engagement: for example, a specific group of providers might be targeted to ask them about their willingness of referring clinical programs to members, the providers' past engagement with members, facilities, and payer can be measured to come up with an index to indicate the provider engagement level.

While certain embodiments of the present invention are described in detail above, the scope of the invention is not to be considered limited by such disclosure, and modifications are possible without departing from the spirit of the invention as evidenced by the following claims:

What is claimed is:

1. A system for predicting and recommending a particular healthcare facility or provider for those members or patients needing a particular medical procedure or other health intervention, the system comprising:

a database for storing historical claims data;

a computer processor;

a graphical user interface comprised of a first region for entering a zip code, and a second region for listing recommended healthcare facilities or providers for performing the particular medical procedure or other health intervention based on the entered zip code;

a non-transitory computer-readable medium storing instructions that when executed by the computer processor cause the computing device to perform the steps of:

a. extracting a heterogeneous graph from the historical claims data, the graph comprised of at least two types of nodes selected from the group comprising a member node, a healthcare facility node, and a provider node, the heterogeneous graph further comprising a plurality of edges each representing a positive class, and a plurality of edges each representing a negative class, wherein each edge representing a positive class connects one member node to one healthcare facility node or provider node that the one member has a previous connection or visit with and wherein each edge representing a negative class connects one member node to one healthcare facility node or provider node that the one member does not have a previous connection or visit with;

b. embedding the heterogeneous graph to generate a member node vector for each member node and a healthcare facility node vector for each healthcare facility node or a provider node vector for each provider node and sampling a neighborhood for each member node and healthcare facility node or provider node and aggregating node feature information from the sampled neighborhood to update each member node vector and each healthcare facility node vector or provider node vector, concatenating a plurality of vectors, each concatenated vector comprised of a first member node vector and at least one healthcare facility node vector or at least one provider node vector, wherein each of the plurality of concatenated vectors represents either a member-healthcare facility pair or member-provider pair;

c. applying a deep learning model to the plurality of concatenated vectors to determine the probability that each member-healthcare facility pair or member-provider pair will be selected for the particular medical procedure or other health intervention, the deep learning model having been trained using labeled member-healthcare-facility pairs or member-provider pairs derived from historical claims data, assigning a positive label where a member previously visited the facility or provider and a negative label where the member did not, and updating model weights by minimizing a loss function; and populating the second region with the recommended healthcare facilities or providers with the highest probabilities for performing the particular medical procedure or other health intervention based on an entered zip code for the patient or member.

2. The system according to claim 1, wherein the heterogeneous graph is further comprised of:

member node features including age, gender and medical conditions; and healthcare facility node features including facility performance and quality.

3. The system according to claim 1, further comprising:

a first model used to score the likelihood that each member would receive the particular medical procedure or other health intervention at the particular type of healthcare facility or with one of the providers before determining the probability that each member-healthcare facility pair or member-provider pair will be selected for the particular medical procedure or other health intervention.

4. The system according to claim 1, wherein the non-transitory computer-readable medium stores instructions that when executed by the computer processor cause the computing device to perform, prior to extracting the graph, a step of generating the plurality of edges where each edge represents a negative class, this step further comprising the steps of:

assigning all available healthcare facilities or providers to each member;

determining a distance between each member location and each healthcare facility location or provider location;

grouping each distance between each member location and each healthcare facility location or provider location into a predetermined number of categories based on the determined distance;

matching each edge representing a positive class with one randomly selected edge representing a negative class from each of the categories; and preparing the graph.

5. The system according to claim 1, wherein the particular medical procedure needed is Esophagogastroduodenoscopy (EGD) and the particular healthcare facility is an Ambulatory Surgery Center (ASC).

6. The system according to claim 1, wherein a weight matrix is applied to the plurality of concatenated vectors to produce final probability scores.

7. The system according to claim 1, wherein the heterogeneous graph is comprised of a training set comprised of a predetermined number of randomly selected member nodes and a testing set comprised of the rest of the member nodes that were not randomly selected for the training set.

8. The system according to claim 1, wherein the graphical user interface is further comprised of a third region for entering in member identification information and a fourth region for entering in a minimum threshold distance that the member-healthcare facility pair or member-provider must fall below.

9. The system according to claim 1, wherein the non-transitory computer-readable medium stores instructions that when executed by the computer processor cause the computing device to generate a neighborhood embedding and concatenate the neighborhood embedding with a respective node vector to update each member node vector and each healthcare facility node vector or provider node vector.

* * * * *